(12) United States Patent
Bernstein et al.

(10) Patent No.: US 7,052,719 B2
(45) Date of Patent: May 30, 2006

(54) MATRICES FORMED OF POLYMER AND HYDROPHOBIC COMPOUNDS FOR USE IN DRUG DELIVERY

(75) Inventors: Howard Bernstein, Cambridge, MA (US); Donald Chickering, Framingham, MA (US); Sarwat Khattak, Cambridge, MA (US); Julie Straub, Winchester, MA (US)

(73) Assignee: Acusphere, Inc., Cambridge, MA (US)

( * ) Notice: Subject to any disclaimer, the term of this patent is extended or adjusted under 35 U.S.C. 154(b) by 951 days.

(21) Appl. No.: 09/731,412

(22) Filed: Dec. 6, 2000

(65) Prior Publication Data

US 2001/0000230 A1 Apr. 12, 2001

Related U.S. Application Data

(62) Division of application No. 09/255,179, filed on Feb. 22, 1999, now Pat. No. 6,423,345.

(60) Provisional application No. 60/083,636, filed on Apr. 30, 1998.

(51) Int. Cl.
| | |
|---|---|
| A61K 9/10 | (2006.01) |
| A61K 9/16 | (2006.01) |
| A61K 47/30 | (2006.01) |
| A61K 47/28 | (2006.01) |
| A61K 47/44 | (2006.01) |

(52) U.S. Cl. ............... 424/501; 424/499; 424/489; 424/486; 424/487; 424/488; 514/951; 514/952

(58) Field of Classification Search .......... 424/486–88, 424/499–502, 430, 434–36, 422–23, 426
See application file for complete search history.

(56) References Cited

U.S. PATENT DOCUMENTS

| | | | |
|---|---|---|---|
| 3,776,001 A | * | 12/1973 | Hanke |
| 4,818,542 A | | 4/1989 | DeLuca et al. |
| 5,342,628 A | | 8/1994 | Picha |
| 5,762,961 A | * | 6/1998 | Roser et al. ............ 424/464 |
| 5,855,913 A | * | 1/1999 | Hanes et al. |
| 5,942,253 A | * | 8/1999 | Gombotz et al. |
| 6,565,885 B1 | | 5/2003 | Tarara et al. |

FOREIGN PATENT DOCUMENTS

| | | |
|---|---|---|
| CA | 2144407 | 3/1994 |
| DE | 43 37 492 A1 | 5/1995 |
| NZ | 231281 | 12/1990 |
| NZ | 264500 | 6/1996 |
| WO | WO 96/03984 A1 | 2/1996 |
| WO | WO 96/15815 | 5/1996 |
| WO | WO 98/04292 A2 | 2/1998 |

OTHER PUBLICATIONS

Beck, et al., "A New Long-Acting Injectable Microcapsule System For The Administration of Progesterone," *Fertility and Sterility* 31(5):545-551 (1979).
Benita, et al., "Characterization of Drug-Loaded Poly(d,l-lactide) Microsheres," *J. Pharmaceutical Sciences* 73(12):1721-1724 (1984).
Federal Register vol. 62, No. 85, pp. 24301-24309 (May 1997).
Mathiowitz, et al., "Morphology of Polyanhydride Microsphere Delivery Systems" *J. Scanning Microscopy* 4(2):329-340(190).
Mathiowitz, et al., "Novel Microcapsules For Delivery Systems" *Reactive Polymers* 6:275-283(1987).

* cited by examiner

*Primary Examiner*—Edward J. Webman
(74) *Attorney, Agent, or Firm*—Pabst Patent Group LLP

(57) ABSTRACT

A lipid or other hydrophobic or amphiphilic compound (collectively referred to herein as "hydrophobic compounds") is integrated into a polymeric matrix for drug delivery to alter drug release kinetics. In embodiments where the drug is water soluble, the drug is released over longer periods of time as compared to release from the polymeric matrix not incorporating the hydrophobic compound into the polymeric material. In contrast to methods in which a surfactant or lipid is added as an excipient, the hydrophobic compound is actually integrated into the polymeric matrix, thereby modifying the diffusion of water into the microparticle and diffusion of solubilized drug out of the matrix. The integrated hydrophobic compound also prolongs degradation of hydrolytically unstable polymers forming the matrix, further delaying release of encapsulated drug.

15 Claims, No Drawings able to $250,000 and must be suitable to the reticuloendothelial system (RES).

MATRICES FORMED OF POLYMER AND HYDROPHOBIC COMPOUNDS FOR USE IN DRUG DELIVERY

This application is a divisional of U.S. Ser. No. 09/255,179 filed Feb. 22, 1999 now U.S. Pat. No. 6,423,345, which claims priority to U.S. Ser. No. 60/083,636 filed Apr. 30, 1998 for "Lipid Polymer Compositions For Enhanced Drug Delivery" by Howard Bernstein, Donald E. Chickering and Julie Ann Straub.

BACKGROUND OF THE INVENTION

The present invention is generally in the area of drug delivery, and is particularly directed to polymer matrices containing drug and having lipid or another hydrophobic or amphiphilic compound incorporated therein to modify the release kinetics. The matrices are preferably used for parenteral delivery. The matrices are preferably in the form of microparticles.

Controlled or sustained release compositions have been developed over the last twenty to thirty years in order to increase the amount of drug delivered by any of a variety of routes, to sustain drug release in a controlled fashion, thereby avoiding burst release which can cause elevated but transient drug levels, and to provide a means for customized release profiles. These formulations have taken many forms, including microparticles such as microspheres and microcapsules formed of drug and encapsulated or mixed with a natural or synthetic polymer, drug particles mixed with excipients such as surfactants to decrease agglomeration of the particles, and devices such as the silastic controlled release depots which release drug as a function of diffusion of water into the device where it dissolves and releases drug back out the same entry. It is difficult to achieve sustained release when the delivery means consists solely of drug or drug and excipient since the drug tends to solubilize relatively quickly. In contrast, non-biodegradable devices such as the silastic devices must be removed after usage.

Microparticles have been formed using a wide range of techniques, including spray drying, hot melt, solvent evaporation, solvent extraction, and mechanical means such as milling and rolling. The microparticles are typically formed of a biocompatible material having desirable release properties as well as being processable by techniques compatible with the drug to be delivered. Many drugs are labile and cannot be encapsulated using harsh organic solvents or heat. Most of these methods result in formation of a structure where drug is released by diffusion of drug out of the microparticle and/or degradation of the microparticle. In some cases it is desirable to further limit or control diffusion.

It is an object of this invention to provide microparticles which have incorporated therein means for limiting diffusion of drug out of the microparticle.

It is a further object of this invention to provide biodegradable microparticles which have incorporated therein means for modifying the degradation kinetics of the microparticles.

It is still another object of the present invention to provide microparticles particularly well suited for parenteral drug delivery.

SUMMARY OF THE INVENTION

A lipid or other hydrophobic or amphiphilic compound (collectively referred to herein as "hydrophobic compounds") is integrated into a polymeric matrix for drug delivery to alter drug release kinetics. In one embodiment where the drug is water soluble, the drug is released over longer periods of time as compared to release from the polymeric matrix not incorporating the hydrophobic compound into the polymeric material. In a further embodiment where the drug has low water solubility, the drug is released over shorter periods of time as compared to release from matrix not incorporating the hydrophobic compound into the polymeric material. In contrast to methods in which a surfactant or lipid is added as an excipient, the hydrophobic compound is actually integrated into the polymeric matrix, thereby modifying the diffusion of water into the microparticle and diffusion of solubilized drug out of the matrix. The integrated hydrophobic compound also prolongs degradation of hydrolytically unstable polymers forming the matrix, further delaying release of encapsulated drug.

The hydrophobic compound must be incorporated into the matrix and the matrix shaped using a technique which results in integration of the hydrophobic compound into the polymeric matrix, rather than at the outer surface of the matrix. In the preferred embodiment, the matrix is formed into microparticles. The microparticles are manufactured with a diameter suitable for the intended route of administration. For example, with a diameter of between 0.5 and 8 microns for intravascular administration, a diameter of 1–100 microns for subcutaneous or intramuscular administration, and a diameter of between 0.5 and 5 mm for oral administration for delivery to the gastrointestinal tract or other lumens. A preferred size for administration to the pulmonary system is an aerodynamic diameter of between one and three microns, with an actual diameter of five microns or more. In the preferred embodiment, the polymers are synthetic biodegradable polymers. Most preferred polymers are biocompatible hydrolytically unstable polymers like polyhydroxy acids such as polylactic acid-co-glycolic acid, polylactide, polyglycolide or polyactide co-glycolide, which may be conjugated to polyethylene glycol or other materials inhibiting uptake by the reticuloendothelial system (RES).

The hydrophobic compounds can be hydrophobic compounds such as some lipids, or amphiphilic compounds (which include both a hydrophilic and hydrophobic component or region). The most preferred amphiphilic compounds are phospholipids, most preferably dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01–60 (w/w polymer), most preferably between 0.1–30 (w lipid/w polymer).

Surface properties of the matrix can also be modified. For example, adhesion can be enhanced through the selection of bioadhesive polymers, which may be particularly desirable when the matrix is in the form of microparticles administered to a mucosal surface such as in intranasal, pulmonary, vaginal, or oral administration. Targeting can also be achieved by selection of the polymer or incorporation within or coupling to the polymer to ligands which specifically bind to particular tissue types or cell surface molecules. Additionally, ligands may be attached to the microparticles which effect the charge, lipophilicity or hydrophilicity of the particle.

DETAILED DESCRIPTION OF THE INVENTION

Methods are provided for the synthesis of polymeric delivery systems consisting of polymer matrices that contain an active agent, such as a therapeutic or prophylactic agent (referred to herein generally as "drug"). The matrices are useful in a variety of drug delivery applications, and can be administered by injection, aerosol or powder, orally, or topically. A preferred route of administration is via the pulmonary system or by injection. The incorporation of a hydrophobic and/or amphiphilic compound (referred to generally herein as "hydrophobic compound") into the polymeric matrix modifies the period of drug release as compared with the same polymeric matrix without the incorporated hydrophobic compound, by altering the rate of diffusion of water into and out of the matrix and/or the rate of degradation of the matrix.

Reagents for Making Matrix Having Hydrophobic Compound Incorporated Therein

As used herein, the term "matrix" refers to a structure including one or more materials in which a drug is dispersed, entrapped, or encapsulated. The material can be crystalline, semi-crystalline, or amorphous. The matrix can be in the form of pellets, tablets, slabs, rods, disks, hemispheres, or microparticles, or be of an undefined shape. As used herein, the term microparticle includes microspheres and microcapsules, as well as microparticles, unless otherwise specified. Microparticles may or may not be spherical in shape. Microcapsules are defined as microparticles having an outer polymer shell surrounding a core of another material, in this case, the active agent. Microspheres are generally solid polymeric spheres, which can include a honeycombed structure formed by pores through the polymer which are filled with the active agent, as described below.

Polymers

The matrix can be formed of non-biodegradable or biodegradable matrices, although biodegradable matrices are preferred, particularly for parenteral administration. Non-erodible polymers may be used for oral administration. In general, synthetic polymers are preferred due to more reproducible synthesis and degradation, although natural polymers may be used and have equivalent or even better properties, especially some of the natural biopolymers which degrade by hydrolysis, such as polyhydroxybutyrate. The polymer is selected based on the time required for in vivo stability, i.e. that time required for distribution to the site where delivery is desired, and the time desired for delivery.

Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred biodegradable polymers include polymers of hydroxy acids such as lactic acid and glycolic acid, and copolymers with PEG, polyanhydrides, poly (ortho)esters, polyurethanes, poly(butyric acid), poly(valeric acid), poly(lactide-co-caprolactone), blends and copolymers thereof.

Examples of preferred natural polymers include proteins such as albumin and prolamines, for example, zein, and polysaccharides such as alginate, cellulose and polyhydroxyalkanoates, for example, polyhydroxybutyrate. The in vivo stability of the matrix can be adjusted during the production by using polymers such as polylactide co glycolide copolymerized with polyethylene glycol (PEG). PEG if exposed on the external surface may elongate the time these materials circulate since it is hydrophilic.

Examples of preferred non-biodegradable polymers include ethylene vinyl acetate, poly(meth)acrylic acid, polyamides, copolymers and mixtures thereof.

Bioadhesive polymers of particular interest for use in targeting of mucosal surfaces, as in the gastrointestinal tract, include polyanhydrides, polyacrylic acid, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly (phenyl methacrylate), poly(methyl acrylate), poly(isopropyl acrylate), poly(isobutyl acrylate), and poly(octadecyl acrylate).

Solvents

A solvent for the polymer is selected based on its biocompatibility as well as the solubility of the polymer and where appropriate, interaction with the agent to be delivered. For example, the ease with which the agent is dissolved in the solvent and the lack of detrimental effects of the solvent on the agent to be delivered are factors to consider in selecting the solvent. Aqueous solvents can be used to make matrices formed of water soluble polymers. Organic solvents will typically be used to dissolve hydrophobic and some hydrophilic polymers. Preferred organic solvents are volatile or have a relatively low boiling point or can be removed under vacuum and which are acceptable for administration to humans in trace amounts, such as methylene chloride. Other solvents, such as ethyl acetate, ethanol, methanol, dimethyl formamide (DMF), acetone, acetonitrile, tetrahydrofuran (THF), acetic acid, dimethyle sulfoxide (DMSO) and chloroform, and combinations thereof, also may be utilized. Preferred solvents are those rated as class 3 residual solvents by the Food and Drug Administration, as published in the Federal Register vol. 62, number 85, pp. 24301–24309 (May 1997).

In general, the polymer is dissolved in the solvent to form a polymer solution having a concentration of between 0.1 and 60% weight to volume (w/v), more preferably between 0.25 and 30%. The polymer solution is then processed as described below to yield a polymer matrix having hydrophobic components incorporated therein.

Hydrophobic and Amphiphilic Compounds

In general, compounds which are hydrophobic or amphiphilic (i.e., including both a hydrophilic and a hydrophobic component or region) can be used to modify penetration and/or uptake of water by the matrix, thereby modifying the rate of diffusion of drug out of the matrix, and in the case of hydrolytically unstable materials, alter degradation and thereby release of drug from the matrix.

Lipids which may be used include, but are not limited to, the following classes of lipids: fatty acids and derivatives, mono-, di and triglycerides, phospholipids, sphingolipids, cholesterol and steroid derivatives, terpenes and vitamins. Fatty acids and derivatives thereof may include, but are not limited to, saturated and unsaturated fatty acids, odd and even number fatty acids, cis and trans isomers, and fatty acid derivatives including alcohols, esters, anhydrides, hydroxy fatty acids and prostaglandins. Saturated and unsaturated fatty acids that may be used include, but are not limited to, molecules that have between 12 carbon atoms and 22 carbon atoms in either linear or branched form. Examples of saturated fatty acids that may be used include, but are not limited to, lauric, myristic, palmitic, and stearic acids. Examples of unsaturated fatty acids that may be used include, but are not limited to, lauric, physeteric, myristoleic, palmitoleic, petroselinic, and oleic acids. Examples of branched fatty acids that may be used include, but are not limited to, isolauric, isomyristic, isopalmitic, and isostearic acids and isoprenoids. Fatty acid derivatives include 12-(((7'-diethylaminocoumarin-3 yl)carbonyl)methylamino)-octadecanoic acid; N-[12-(((7'diethylaminocoumarin-3-yl) carbonyl)methyl-amino) octadecanoyl]-2-aminopalmitic acid, N succinyl-dioleoylphosphatidylethanol amine and palmitoyl-homocysteine; and/or combinations thereof. Mono, di and triglycerides or derivatives thereof that may be used include, but are not limited to, molecules that have fatty acids or mixtures of fatty acids between 6 and 24 carbon atoms, digalactosyldiglyceride, 1,2-dioleoyl-sn-glycerol; 1,2-cdipalmitoyl-sn-3 succinylglycerol; and 1,3-dipalmitoyl-2-succinylglycerol.

Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

Sphingolipids which may be used include ceramides, sphingomyelins, cerebrosides, gangliosides, sulfatides and lysosulfatides. Examples of Sphinglolipids include, but are not limited to, the gangliosides GM1 and GM2.

Steroids which may be used include, but are not limited to, cholesterol, cholesterol sulfate, cholesterol hemisuccinate, 6-(5-cholesterol 3β-yloxy) hexyl-6-amino-6-deoxy-1-thio-α-D-galactopyranoside, 6-(5-cholesten-3β-tloxy) hexyl-6-amino-6-deoxyl-1-thio-α-D mannopyranoside and cholesteryl)4'-trimethyl 35 ammonio)butanoate.

Additional lipid compounds which may be used include tocopherol and derivatives, and oils and derivatized oils such as stearylamine.

A variety of cationic lipids such as DOTMA, N-[1-(2,3-dioleoyloxy)propyl-N,N,N-trimethylammonium chloride; DOTAP, 1,2-dioleoyloxy-3-(trimethylammonio) propane; and DOTB, 1,2-dioleoyl-3-(4'-trimethyl-ammonio) butanoyl-sn glycerol may be used.

The most preferred lipids are phospholipids, preferably DPPC, DAPC, DSPC, DTPC, DBPC, DLPC and most preferably DPPC, DAPC and DBPC.

Other preferred hydrophobic compounds include amino acids such as tryptophane, tyrosine, isoleucine, leucine, and valine, aromatic compounds such as an alkyl paraben, for example, methyl paraben, and benzoic acid.

The content of hydrophobic compound ranges from 0.01–60 (w hydrophobic compound/w polymer); most preferably between 0.1–30 (w hydrophobic compound/w polymer).

Targeting

Microparticles can be targeted specifically or non-specifically through the selection of the polymer forming the microparticle, the size of the microparticle, and/or incorporation or attachment of a ligand to the microparticles. For example, biologically active molecules, or molecules affecting the charge, lipophilicity or hydrophilicity of the particle, may be attached to the surface of the microparticle. Additionally, molecules may be attached to the microparticles which minimize tissue adhesion, or which facilitate specific targeting of the microparticles in vivo. Representative targeting molecules include antibodies, lectins, and other molecules which are specifically bound by receptors on the surfaces of cells of a particular type.

Inhibition of Uptake by the RES

Uptake and removal of the microparticles can be minimized through the selection of the polymer and/or incorporation or coupling of molecules which minimize adhesion or uptake. For example, tissue adhesion by the microparticle can be minimized by covalently binding poly(alkylene glycol) moieties to the surface of the microparticle. The surface poly(alkylene glycol) moieties have a high affinity for water that reduces protein adsorption onto the surface of the particle. The recognition and uptake of the microparticle by the reticulo-endothelial system (RES) is therefore reduced.

In one method, the terminal hydroxyl group of the poly (alkylene glycol) is covalently attached to biologically active molecules, or molecules affecting the charge, lipophilicity or hydrophilicity of the particle, onto the surface of the microparticle. Methods available in the art can be used to attach any of a wide range of ligands to the microparticles to enhance the delivery properties, the stability or other properties of the microparticles in vivo.

Active Agents

Active agents which can be incorporated into the matrix for delivery include therapeutic or prophylactic agents. These can be proteins or peptides, sugars, oligosaccharides, nucleic acid molecules, or other synthetic or natural agents.

The agents may be labeled with a detectable label such as a fluorescent label or an enzymatic or chromatographically detectable agent.

Preferred drugs include antibiotics, antivirals, vaccines, vasodilators, vasoconstrictors, immunomodulatory compounds, including steroids, antihistamines, and cytokines such as interleukins, colony stimulating factors, tumor necrosis factor and interferon ($\alpha$, $\beta$, $\gamma$), oligonucleotides including genes and antisense, nucleases, bronchodilators, hormones including reproductive hormones, calcitonin, insulin, erthropoietin, growth hormones, and other types of drugs such as Antiban™.

Methods for Manufacture of Matrix

In the most preferred embodiment, microparticles are produced by spray drying. Techniques which can be used to make other types of matrices, as well as microparticles, include melt extrusion, compression molding, fluid bed drying, solvent extraction, hot melt encapsulation, and solvent evaporation, as discussed below. A major criteria is that the hydrophobic compound must be dissolved or melted with the polymer or dispersed as a solid or a liquid in a solution of the polymer, prior to forming the matrix. As a result, the hydrophobic (or amphiphilic) compound is mixed throughout the matrix, in a relatively uniform manner, not just on the surface of the finished matrix. The active agent can be incorporated into the matrix as solid particles, as a liquid or liquid droplets, or by dissolving the agent in the polymer solvent.

a. Solvent Evaporation. In this method the polymer and hydrophobic compound are dissolved in a volatile organic solvent such as methylene chloride. A pore forming agent as a solid or as a liquid may be added to the solution. The active agent can be added as either a solid or in solution to the polymer solution. The mixture is sonicated or homogenized and the resulting dispersion or emulsion is added to an aqueous solution that may contain a surface active agent such as TWEEN™ 20, TWEEN™ 80, PEG or poly(vinyl alcohol) and homogenized to form an emulsion. The resulting emulsion is stirred until most of the organic solvent evaporates, leaving microparticles. Several different polymer concentrations can be used (0.05–0.60 g/ml). Microparticles with different sizes (1–1000 microns) and morphologies can be obtained by this method. This method is particularly useful for relatively stable polymers like polyesters.

Solvent evaporation is described by E. Mathiowitz, et al., *J. Scanning Microscopy*, 4, 329 (1990); L. R. Beck, et al., *Fertil. Steril.*, 31, 545 (1979); and S. Benita, et al., *J. Pharm. Sci.*, 73, 1721 (1984), the teachings of which are incorporated herein.

Particularly hydrolytically unstable polymers, such as polyanhydrides, may degrade during the fabrication process due to the presence of water. For these polymers, the following two methods, which are performed in completely organic solvents, are more useful.

b. Hot Melt Microencapsulation. In this method, the polymer and the hydrophobic compound are first melted and then mixed with the solid or liquid active agent. A pore forming agent as a solid or in solution may be added to the solution. The mixture is suspended in a non-miscible solvent (like silicon oil), and, while stirring continuously, heated to 5° C. above the melting point of the polymer. Once the emulsion is stabilized, it is cooled until the polymer particles solidify. The resulting microparticles are washed by decantation with a polymer non-solvent such as petroleum ether to give a free-flowing powder. Microparticles with sizes between one to 1000 microns can be obtained with this method. The external surfaces of particles prepared with this technique are usually smooth and dense. This procedure is used to prepare microparticles made of polyesters and polyanhydrides. However, this method is limited to polymers with molecular weights between 1000–50,000.

Hot-melt microencapsulation is described by E. Mathiowitz, et al., *Reactive Polymers*, 6, 275 (1987), the teachings of which are incorporated herein. Preferred polyanhydrides include polyanhydrides made of bis-carboxyphenoxypropane and sebacic acid with molar ratio of 20:80 (P(CPP-SA) 20:80) (Mw 20,000) and poly(fumaric-co-sebacic) (20:80) (MW 15,000) microparticles.

c. Solvent Removal. This technique was primarily designed for polyanhydrides. In this method, the solid or liquid active agent is dispersed or dissolved in a solution of the selected polymer and hydrophobic compound in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. The external morphology of particles produced with this technique is highly dependent on the type of polymer used.

d. Spray Drying of Microparticles. Microparticles can be produced by spray drying by dissolving a biocompatible polymer and hydrophobic compound in an appropriate solvent, dispersing a solid or liquid active agent into the polymer solution, and then spray drying the polymer solution, to form microparticles. As defined herein, the process of "spray drying" a solution of a polymer and an active agent refers to a process wherein the solution is atomized to form a fine mist and dried by direct contact with hot carrier gases. Using spray drying apparatus available in the art, the polymer solution may be delivered through the inlet port of the spray drier, passed through a tube within the drier and then atomized through the outlet port. The temperature may be varied depending on the gas or polymer used. The temperature of the inlet and outlet ports can be controlled to produce the desired products.

The size of the particulates of polymer solution is a function of the nozzle used to spray the polymer solution, nozzle pressure, the flow rate, the polymer used, the polymer concentration, the type of solvent and the temperature of spraying (both inlet and outlet temperature) and the molecular weight. Generally, the higher the molecular weight, the larger the particle size, assuming the concentration is the same. Typical process parameters for spray drying are as follows: polymer concentration=0.005–0.20 g/ml, inlet temperature=20–1000° C., outlet temperature=10–300° C., polymer flow rate=5–2000 ml/min., and nozzle diameter=0.2–4 mm ID. Microparticles ranging in diameter between one and ten microns can be obtained with a morphology which depends on the selection of polymer, concentration, molecular weight and spray flow.

If the active agent is a solid, the agent may be encapsulated as solid particles which are added to the polymer solution prior to spraying, or the agent can be dissolved in an aqueous solution which then is emulsified with the polymer solution prior to spraying, or the solid may be cosolubilized together with the polymer in an appropriate solvent prior to spraying.

e. Hydrogel Microparticles. Microparticles made of gel-type polymers, such as polyphosphazene or polymethylmethacrylate, are produced by dissolving the polymer in an aqueous solution, suspending if desired a pore forming agent and suspending a hydrophobic compound in the mixture, homogenizing the mixture, and extruding the material through a microdroplet forming device, producing microdroplets which fall into a hardening bath consisting of an oppositely charged ion or polyelectrolyte solution, that is slowly stirred. The advantage of these systems is the ability to further modify the surface of the microparticles by coating them with polycationic polymers, like polylysine after fabrication. Microparticle particles are controlled by using various size extruders.

Additives to Facilitate Matrix Formation

A variety of surfactants may be added to the continuous phase as emulsifiers if one is used during the production of the matrices. Exemplary emulsifiers or surfactants which may be used (0.1–5% by weight) include most physiologically acceptable emulsifiers. Examples include natural and synthetic forms of bile salts or bile acids, both conjugated with amino acids and unconjugated such as taurodeoxycholate, and cholic acid. In contrast to the methods described herein, these surfactant will coat the microparticle and will facilitate dispersion for administration.

Pore Forming Agents

Pore forming agents can be included in an amount of between 0.01% and 90% weight to volume, to increase matrix porosity and pore formation during the production of the matrices. The pore forming agent can be added as solid particles to the polymer solution or melted polymer or added as an aqueous solution which is emulsified with the polymer solution or is co-dissolved in the polymer solution. For example, in spray drying, solvent evaporation, solvent removal, hot melt encapsulation, a pore forming agent such as a volatile salt, for example, ammonium bicarbonate, ammonium acetate, ammonium chloride or ammonium benzoate or other lyophilizable salt, is first dissolved in water. The solution containing the pore forming agent is then emulsified with the polymer solution to create droplets of the pore forming agent in the polymer. This emulsion is then spray dried or taken through a solvent evaporation/extraction process. After the polymer is precipitated, the hardened microparticles can be frozen and lyophilized to remove any pore forming agents not removed during the microencapsulation process.

Methods for Administration of Drug Delivery Systems

The matrix can be administered orally, topically, to a mucosal surface (i.e., nasal, pulmonary, vaginal, rectal), or by implantation or injection, depending on the form of the matrix and the agent to be delivered. Useful pharmaceutically acceptable carriers include saline containing glycerol and TWEEN™ 20 and isotonic mannitol containing TWEEN™ 20. The matrix can also be in the form of powders, tablets, in capsules, or in a topical formulation such as an ointment, gel or lotion.

Microparticles can be administered as a powder, or formulated in tablets or capsules, suspended in a solution or in a gel (ointment, lotion, hydrogel). As noted above, the size of the microparticles is determined by the method of administration. In the preferred embodiment, the microparticles are manufactured with a diameter of between 0.5 and 8 microns for intravascular administration, a diameter of 1–100 microns for subcutaneous or intramuscular administration, and a diameter of between 0.5 and 5 mm for oral administration for delivery to the gastrointestinal tract or other lumens, or application to other mucosal surfaces (rectal, vaginal, oral, nasal). A preferred size for administration to the pulmonary system is an aerodynamic diameter of between one and three microns, with an actual diameter of five microns or more, as described in U.S. Pat. No. U.S. Pat. No. 5,855,913, which issued on Jan. 5, 1999, to Edwards, et al. Particle size analysis can be performed on a Coulter counter, by light microscopy, scanning electron microscopy, or transmittance electron microscopy.

In the preferred embodiment, microparticles are combined with a pharmaceutically acceptable carrier such as phosphate buffered saline or saline or mannitol, then an effective amount administered to a patient using an appropriate route, typically by injection into a blood vessel (i.v.), subcutaneously, intramuscularly (IM) or orally. Microparticles containing an active agent may be used for delivery to the vascular system, as well as delivery to the liver and renal systems, in cardiology applications, and in treating tumor masses and tissues. For administration to the pulmonary system, the microparticles can be combined with pharmaceutically acceptable bulking agents and administered as a dry powder. Pharmaceutically acceptable bulking agents include sugars such as mannitol, sucrose, lactose, fructose and trehalose. The microparticles also can be linked with ligands that minimize tissue adhesion or that target the microparticles to specific regions of the body in vivo as described above.

The methods and compositions described above will be further understood with reference to the following non-limiting examples.

EXAMPLE 1

Preparation of PLGA:DAPC Drug Delivery Particles 30 grams of PLGA (50:50) (IV 0.4 dL/g Boehringer Ingelheim), 1.8 g of diarachidoylphosphatidylcholine (Avanti, Birmingham, Ala.) and 495 mg of Azure A (Sigma Chemicals, St. Louis, Mo.) were dissolved in 1000 ml of methylene chloride. The solution was pumped at a flowrate of 20 mL/min and spray dried using a Bucchi Lab spray dryer. The inlet air temperature was 40° C. The dried microparticle powder was collected and stored at −20° C. until analysis. Size of the microparticles was performed using a Coulter multisizer II. The microparticles have a volume average mean diameter of 5.982 microns.

18 grams of PLGA (50:50) (IV 0.4 dL/g Boehringer Ingelheim) and 1.08 g of diarachidoylphosphatidylcholine (Avanti, Birmingham, Ala.) were dissolved in 600 mL of methylene chloride. 38.9 mg of Eosin Y (Sigma Chemicals) was dissolved in 38.9 mL of a 0.18 g/ml ammonium bicarbonate solution. The eosin solution was emulsified with the polymer solution using a Silverson homogenizer at 7000 rpm for 8 minutes. The solution was pumped at a flowrate of 20 mL/min and spray dried using a Bucchi Lab spray dryer. The inlet air temperature was 40° C. The dried microparticle powder was collected and stored at −20° C. until analysis. Size analysis of the microparticles was performed using a Coulter multisizer II. The microparticles have a volume average mean diameter of 6.119 microns.

Modifications and variations of the present invention will be obvious to those skilled in the art from the foregoing detailed description and are intended to come within the scope of the following claims.

We claim:

1. A method for administering a therapeutic or prophylactic agent comprising administering to a patient a matrix for delivery of a therapeutic or prophylactic agent,
   wherein the matrix is formed of a biocompatible polymer having incorporated therein an therapeutic or prophylactic agent and an effective amount of a hydrophobic or amphiphilic compound to modify the diffusion of water into the matrix and the release of the therapeutic or prophylactic agent from the matrix, wherein the drug is released over shorter periods of time as compared to release from matrices not incorporating the hydrophobic or amphiphilic compound, the matrix being formed by a method comprising emulsifying a polymer solution, the therapeutic or prophylactic agent, a hydrophobic or amphiphilic compound, and a pore forming agent, then removing the solvent and the pore forming agent to produce a matrix.

2. The method of claim 1 wherein the matrix is in the form of microparticles.

3. The method of claim 1 wherein the hydrophobic or amphiphilic compound is incorporated into the matrix at a ratio of between 0.01 and 60 by weight of hydrophobic compound to weight of polymer.

4. The method of claim 1 wherein the hydrophobic or amphiphilic compound is a lipid incorporated into the matrix at a ratio of between 0.01 and 30 (weight lipid/weight matrix material).

5. The method of claim 4 wherein the lipid is selected from the group consisting of fatty acids and derivatives, mono-, di and triglycerides, phospholipids, sphingolipids, cholesterol and steroid derivatives, oils, vitamins and terpenes.

6. The method of claim 5 wherein the lipid is a phospholipid selected from the group consisting of phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids.

7. The method of claim 6 wherein the phospholipid is selected from the group consisting of dioleoylphosphatidylcholine, dimyristoylphosphatidylcholine, dipentadecanoylphosphatidylcholine, dilauroylphosphatidylcholine, dipalmitoylphosphatidylcholine, distearoylphosphatidylcholine, diarachidoylphosphatidylcholine, dibehenoylphosphatidylcholine, ditricosanoylphosphatidylcholine, dilignoceroylphatidylcholine; and phosphatidylethanolamines.

8. The method of claim 1 wherein the agent is a therapeutic agent.

9. The method of claim 1 wherein the matrix is formed of a bioadhesive polymer.

10. The method of claim 1 wherein the matrix is formed of a polymer selected from the group consisting of poly (hydroxy acids), polyanhydrides, polyorthoesters, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polysiloxanes, poly(vinyl alcohols), poly(vinyl acetate), polystyrene, polyurethanes and co-polymers thereof, synthetic celluloses, polyacrylic acids, poly(butyric acid), poly(valeric acid), and poly(lactide-co-caprolactone), ethylene vinyl acetate, copolymers and blends thereof.

11. The method of claim 1 wherein the matrix is formed of a protein or polysaccharide.

12. The method of claim 1 wherein the matrix is in a pharmaceutically acceptable carrier for topical application or application to a mucosal surface.

13. The method of claim 1 wherein the matrix is in a pharmaceutically acceptable carrier for injection.

14. The method of claim 1 wherein the matrix is formulated for administration rectally or vaginally.

15. The method of claim 2 wherein the microparticles are formulated for pulmonary administration.

* * * * *

UNITED STATES PATENT AND TRADEMARK OFFICE
CERTIFICATE OF CORRECTION

PATENT NO. : 7,052,719 B2  Page 1 of 1
APPLICATION NO. : 09/731412
DATED : May 30, 2000
INVENTOR(S) : Howard Bernstein et al.

It is certified that error appears in the above-identified patent and that said Letters Patent is hereby corrected as shown below:

Claim 1, column 10, line 64, replace "an" with --a--.
Claim 1, column 11, line 7, delete "a".

Signed and Sealed this

Sixteenth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,052,719 B2  Page 1 of 1
APPLICATION NO. : 09/731412
DATED : May 30, 2006
INVENTOR(S) : Howard Bernstein et al.

It is certified that error appears in the above-identified patent and that said Letters Patent is hereby corrected as shown below:

Claim 1, column 10, line 64, replace "an" with --a--.
Claim 1, column 11, line 7, delete "a".

This certificate supersedes Certificate of Correction issued October 16, 2007.

Signed and Sealed this

Thirteenth Day of November, 2007

JON W. DUDAS
*Director of the United States Patent and Trademark Office*